United States Patent [19]

Sugiyama et al.

[11] Patent Number: 4,728,432
[45] Date of Patent: Mar. 1, 1988

[54] METHOD FOR DECONTAMINATING BLOOD

[75] Inventors: Masafumi Sugiyama; Hideki Kawanishi, both of Hiroshima, Japan

[73] Assignee: Japan Medical Supply Co., Ltd., Hiroshima, Japan

[21] Appl. No.: 863,470

[22] Filed: May 14, 1986

Related U.S. Application Data

[63] Continuation-in-part of Ser. No. 667,410, Nov. 5, 1984, abandoned, which is a continuation of Ser. No. 514,842, Jul. 18, 1983, abandoned.

[30] Foreign Application Priority Data

Aug. 10, 1982 [JP] Japan ................... 57-137914

[51] Int. Cl.⁴ .................. B01D 13/00; B01D 15/00
[52] U.S. Cl. ................... 210/646; 210/651; 210/679; 210/691; 210/692; 210/694
[58] Field of Search ............ 210/638, 645, 650, 651, 210/679, 691, 692, 694, 321.3, 433.2, 500.21, 502.1, 503–509, 927, 646

[56] References Cited

U.S. PATENT DOCUMENTS

| | | | |
|---|---|---|---|
| 3,238,056 | 3/1966 | Pall et al. | 210/505 |
| 3,800,945 | 4/1974 | Fowler | 210/505 |
| 3,983,053 | 9/1976 | Courtney et al. | 210/679 |
| 4,209,392 | 6/1980 | Wallace | 210/321.3 |
| 4,384,954 | 5/1983 | Nakashima et al. | 210/927 |

Primary Examiner—Ivars Cintins
Attorney, Agent, or Firm—Kramer, Brufsky & Cifelli

[57] ABSTRACT

A method for decontaminating blood uses an adsorber prepared by forming a porous membrane containing an adsorbent in the form of powder or fine particles on a support is suitable for removing harmful soluble substances contained in blood. The adsorber has a high rate of adsorbtion, and does not readily shed the fine particles of the adsorbent material. In order to attain these features, it is necessary to set the thickness of the porous membrane within a specified range.

17 Claims, 4 Drawing Figures

METHOD FOR DECONTAMINATING BLOOD

CROSS REFERENCE TO RELATED APPLICATIONS

This application is a continuation-in-part of copending application Ser. No. 667,410 filed Nov. 5, 1984 which, in turn, is a continuation of application Ser. No. 514,842 filed July 18, 1983, both now abandoned.

BACKGROUND OF THE INVENTION

This invention relates to an adsorber for hemoperfusion to remove soluble poisonous substances contained in blood by means of adsorption.

Patients of renal failure or liver failure suffer reduced ability to excrete soluble poisonous substances such as creatinine, uric acid, urea and protein-bound substances from their blood, resulting in an accumulation of such poisonous substances in their blood which endangers their lives. To prevent this, dialysis or use of adsorbents has heretofore been employed to remove these poisonous substances and thereby decontaminate the blood. However, since dialysis is a means of decontamination using a semipermeable membrane, it is rather difficult to effectively remove substances of middle or large molecules and protein-bound substances represented by bilirubin.

Another means of decontamination is to bring an adsorbent into direct contact with blood to adsorb poisonous substances, allowing various poisonous substances to be removed from blood if the type of adsorbent is selected properly. With this type of decontamination, the adsorption of poisonous substances contained in blood is carried out by liquid phase adsorption. In general, it is desirable to use an adsorbent in the form of powder or fine particles having a large surface area, because substances have a smaller diffusion velocity in the liquid phase than in the gaseous phase, and the adsorption velocity is consequently dependent on the surface area of the adsorbent. However, adsorbents in the form of fine particles having a large surface area cannot be safely used, because they would flow into the human body. Thus, in order to effectively decontaminate blood by the use of an adsorbent in the form of powder or fine particles, it becomes essential to fix the adsorbent by some effective means. Several methods have been proposed for mixing a high-molecular weight material and an adsorbent and fixing them into a spherical or membraneous form, as described in *Artificial Organs*, Vol. 4, 302 (1980) and Vol. 6, 151 (1982) and Japanese Patent Publication No. 32636/1978. These methods are inadequate because the ratio of the high-molecular weight material to the absorbent has to be great enough to adequately maintain such a fixed state, with the result being that the high-molecular weight material layer on the surface of the adsorbent will become thicker and the adsorptivity will be greatly reduced.

A method of using a particulate adsorbent coated with a thin layer of a high-molecular weight material has been proposed in Japanese Patent Publication Nos. 3944/1980 and 27090/1981. This method is still inadequate because poisonous substances are transformed so slowly into the adsorbent that a satisfactory adsorption velocity can hardly be expected.

SUMMARY OF THE INVENTION

An object of the present invention is to provide an adsorber which exhibits significant adsorption velocity and does not allow the adsorbent to intrude into the human body.

Another object of the invention is to provide an adsorber having an excellent compatability with blood.

A further object is to provide an adsorber ensuring little pressure loss on the adsorber layer when the blood flows thereacross.

A still further object is to provide an adsorber for hemoperfusion to remove soluble poisonous substances contained in blood by means of adsorption.

The adsorber of this invention consists of a 10 to 400 (micron) thick porous membrane containing an adsorbent in the form of powder or fine particles and a support. The support is used to increase the strength of the whole adsorber, so that the adsorber can assure a practically sufficient strength, even when the high-molecular weight material for fixing the adsorbent is used in a decreased amount. Thus, a high adsorption velocity can be obtained because the high-molecular weight material is used in a small amount.

DETAILED DESCRIPTION OF THE INVENTION

The adsorbents which can be used in this invention are, for example, activated carbon, porous resins, porous alumina, porous silica, porous glass, ion exchange resins, etc. These adsorbents should be selected properly, depending on the substances which are to be removed from blood by adsorption. The adsorbent has to be in the form of powder or fine particles, whereby a high adsorption velocity can be obtained. The suitable average particle diameter of the adsorbent is 10 to 100$\mu$.

Figure 1:
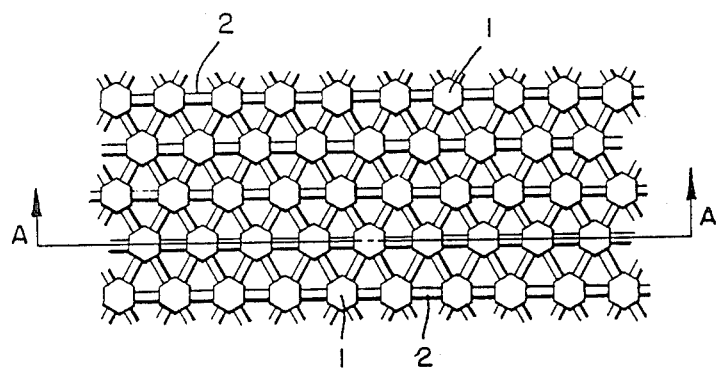
FIG. 1 is a diagram showing a front view of an embodiment of the support used for the adsorber of this invention.
Figure 2:
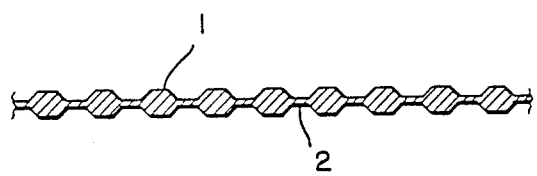
FIG. 2 is a diagram showing the cross section of the support shown in FIG. 1.

The support of this invention is used for fixing the adsorbent. it may be in the form of film, sheet, mesh, woven cloth, nonwoven cloth or any other form, preferably one comprising a net or having ruggedness on its surface as to keep the blood ciculating under good condition. The most desirable support is one having a net structure and consisting of thick particulate portions and thin linear portions. Normally, the adsorber is used in multiple layers. The superposed adsorber layers, each of which is provided with a support having a structure as described above, will retain a suitable space between one another without clinging to each other, so that the entire adsorber will admit the blood in a uniform flow, whereby a high adsorption velocity can be obtained and the pressure loss can be minimized. Moreover, the fact that a large surface area is obtained is advantageous in respect of adsorption velocity. Examples of such a support are given in FIGS. 1 and 2. FIG. 1 is a diagram showing an enlarged front view of the support, and FIG. 2 is a section along line A—A of the support in FIG. 1. In the Figures, 1 is a thick particulate portion and 2 is a thin linear portion. Preferably, the thick portions should have a thickness ranging from 40 to 500$\mu$ and the thin portions from 3 to 30$\mu$. The net structure should have a void content ranging from 30 to 80%. If the void content is smaller than 30%, the pressure loss will increase, while if it is greater than 80%, the amount of the adsorbent to be fixed will decrease. The diameter of the thick portions is preferably in the range from 50 to 1,000$\mu$, and the width of the thin portions from 5 to 500$\mu$, although these dimensions need not be particularly specified. The thick portions should be present in a density of 10 to 200/cm$^2$.

The above-mentioned support can be prepared by known methods. For instance, the method set forth in Japanese Patent Laid-Open No. 38977/1979 is convenient for the present purpose. The support thus prepared is scattered with polygonal or circular thick portions, from which thin portions are extended radially and connected to thick portions (see FIG. 1).

The materials for the support are, for example, high-molecular weight substances such as polyethylene, polypropylene, nylon, polyester and cellulose, metals and ceramics; above all, high-molecular weight substances are advantageous in respect to their handling characteristics and easy processability. Moreover, it is desirable for the support to have a tensile strength of 0.2 kg/cm or greater in practical use.

The adsorber of this invention consists of a porous membrane containing an adsorbent in the form of powder or fine particles which is fixed on the support. This adsorber can be prepared by the known method of producing porous membranes as follows: a polymer solution containing the adsorbent dispersed therein is applied to the support by means of flowcasting, dipping, coating or spraying, and the dispersion is then placed into contct with a non-solvent (i.e. a liquid in which the dispersion is substantially insoluble) for solidifying the polymer and extracting the solvent. The porous membrane containing the adsorbent is then fixed on the support. It is also possible to prepare the adsorber by applying a molten polymer, containing the adsorbent and extractable additives dispersed therein, to the support, solidifying the polymer, and subsequently extracting the additives, thereby providing a porous structure.

The polymers capable of forming a porous membrane are, for example, polyurethane, polysulfone, polystyrene, polyamide, polyethylene, polypropylene, polyvinyl alcohol, polyhydroxyethyl methacrylate and cellulose.

Though the content of the adsorbent in the adsorber is not particularly specified, normally it should be in the range from 30 to 70 wt %, in view of the fact that its adsorption capacity will decrease when its content is too low, and that fine particles will increasingly occur when its content is too high.

In this invention, the porous membrane fixed on the support is required to have a thickness ranging from 10 to 400$\mu$. In case the membrane thickness is greater than 400$\mu$, the adsorbent will not be dispersed uniformly inside the porous membrane, so that its density distribution will become uneven in some portions of the adsorber. As a result, the diffusion of the adsorbed substances inside will become slower, and both the adsorption velocity and the adsorption capacity will decrease. On the other hand, if the membrane thickness is smaller than 10$\mu$, the membrane strength will decrease, and it is possible that the membrane will be injured while in use. Such damage to the membrane would allow the adsorbent to be mixed with the blood and flow into the body, and could cause blood platelets to adhere to the surface of the adsorber. The membrane thickness herein means the thickness on one side of the support in cases where the support is in the form of a film or a sheet and the porous membrane is fixed on one side or both sides of the support. However, in cases where the support has a net structure and the porous membrane has both sides linked across the net, the membrane thickness means the overall thickness.

Normally, the adsorber of this invention is used by rolling or superposing it into multiple layers and housing it in a vessel having an inlet and an outlet for the blood. The adsorber may be contacted with the whole blood or with plasma or serum alone.

The adsorber of the present invention is especially useful in removing soluble poisonous substances contained in the blood such as creatinine, uric acid, urea and protein-bound substances such as bilirubin, by hemoperfusion.

Figure 3:
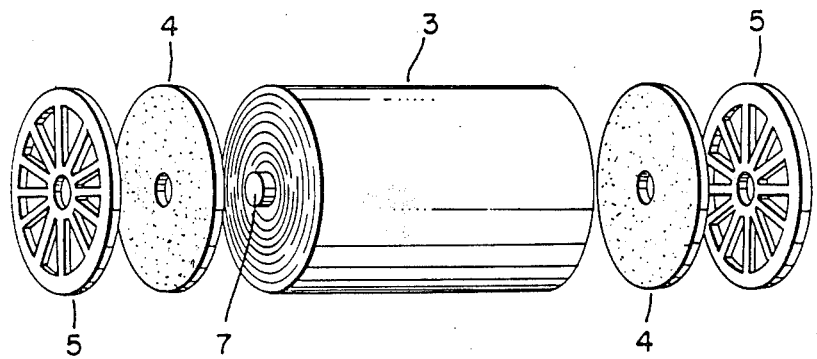
FIG. 3 is an example of the components of hemoperfusion equipment having a built-in adsorber according to this invention.

FIG. 3 is an exploded view showing the disassembled components of a hemoperfusion device using the adsorber of this invention, prior to assembly in a housing vessel (not shown).

Figure 4:
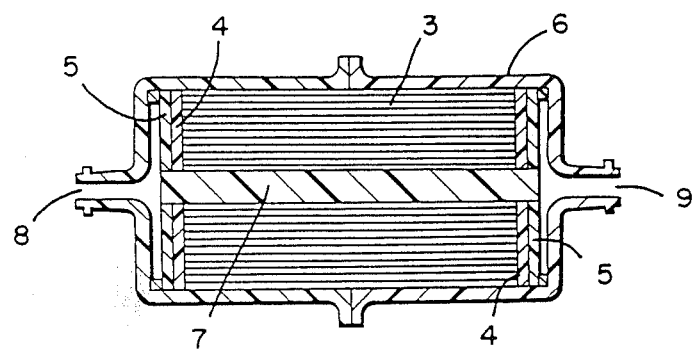
FIG. 4 is a cross section of the assembly of the components of FIG. 3.

FIG. 4 shows a cross section of the assembled equipment. In these Figures, 3 is a rolled adsorber containing an adsorbent in the form of powder or fine particles fixed on a mesh support, 4 is an elastomer provided on both ends of said adsorber, 5 is an end support provided on both sides of the elastomer to hold the adosrber and the elastomer, 6 is a vessel to house items 3-5, and 7 is a core.

The elastomer is provided to protect the end portions of the adsorber, and has a porous structure so as not to interfere with the blood passage. More precisely, it can be an open-cell foam consisting of a high-molecular weight material such as polyurethane or silicone. Since the device is provided with the elastomer, the fine adsorbent particles can be prevented to a large extent from exiting from the end portions of the adsorber and they can therefore serve effectively for hemoperfusion. The elastomer should be circular, oval, square or oblong in shape, corresponding to the shape of the end portion of the adsorber.

In the embodiment illustrated, the elastomer is provided with an end support on both sides. The end support should consist of a rigid material and have a structure for holding the adsorber and the elastomer entirely and creating space for blood passage, such as porous board or a structure shown in FIG. 1. The end support enables the elastomer to uniformly adhere to the entire end portion of the adsorber, so that the elastomer will be effective across its entire surface. The support is preferably made of a plastic material such as polyethylene, polypropylene or polycarbonate. Alternatively, metals or ceramics may be used.

The hemoperfusion device is thus built by assembling the above-mentioned adsorber, elastomer and end support and housing them in the vessel having an inlet and an outlet for the blood. The housing vessel 6 is provided with a blood inlet 8 and outlet 9. The vessel can be made of various plastic materials such as polystyrene, polypropylene or polycarbonate, metals, glass, ceramics, etc., and may be composed of two or more portions as necessary.

The hemoperfusion device should be sterilized prior to use, by means of steam or $\gamma$ ray irradiation.

EXAMPLES

Example 1

10 g of powdery activated carbon (particle diameter of 40μ or less) was mixed with 50 ml of a polyurethane solution (a solution of 10 w/v % polyurethane in tetrahydrofuran) to give a suspension, which was allowed to flow over both sides of a polyethylene support (thick portions 140~160μ in thickness, thin portions 8~12μ in thickness, thick portions 90~100/cm² in number, void content 40~45%, and tensile strength 0.6~0.8 kg/cm wid.) which has a net structure as shown in FIGS. 1 and 2, whereby a 200μ thick membrane was prepared. The membrane was then dipped in water, so as to extract the tetrahydrofuran contained therein. It was further freed of the solvent completely by dipping in hot water at 80° C. to give an adsorber having a 200μ thick porous membrane. The adsorber thus obtained had an activated carbon content of 65%, with a lot of fine holes, 1-6μ in diameter, on the polyurethane layer.

For comparison, an adsorber having a 500μ thick porous membrane was prepared using a polypropylene mesh support by the same method as described above.

In the present experiment, mongrel grown-up dogs were caused to suffer from jaundice with their common bile duct ligated, and after three to four weeks their serum was collected as a test solution for the measurement of the adsorptivity of the two different adsorbers prepared as above, powdery activated carbon and granular activated carbon. In testing, 0.25 g of each adsorber or adsorbent was added to 50 ml each of the test solution, and the mixture was stirred at 37° C. and 120 cpm for 120 minutes to measure the total bilirubin concentrations before and after the adsorption test. The results are shown in Table 1.

TABLE 1

| | Bilirubin concentration (mg/d) | | |
|---|---|---|---|
| | before adsorption | after adsorption | Adsorption rate % |
| Adsorber (200 thick) | 10.5 | 4.7 | 55.2 |
| Adsorber (500 thick) | " | 8.0 | 23.5 |
| Powdery activated carbon | " | 3.3 | 68.6 |
| Granular activated carbon | " | 9.5 | 9.5 |

As shown in Table 1, the 200μ thick adsorber in this invention exhibited an adsorption rate close to that of powdery activated carbon. However, the 500 thick porous membrane afforded a rate of adsorption which was only about a half of the value obtained with the 200μ thick membrane, and it is evident that the adsorptivity is affected greatly by the thickness of porous membrane.

Example 2

100 g of powdery activated carbon (particle diameter of 10~40μ) was mixed with 500 ml of a polyurethane solution (a solution of 10 w/v % polyurethane in tetrahydrofuran) to give a suspension, which was allowed to flow over both sides of a polyethylene support (thick portions 140~160μ in thickness, thin portions 8~12μ in thickness, thick portions 90~100/cm² in number, void content 40~45%, and tensile strength 0.6~0.8 kg/cm wid.) which has a net structure as shown in FIGS. 1 and 2, whereby a 200μ thick membrane was prepared. The membrane was then dipped in water so as to extract the tetrahydrofuran contained therein. It was further freed of the solvent completely by dipping in hot water at 80° C. to give an adsorber. The adsorber thus obtained had an activated carbon content of 65%, with alot of fine holes, 1~6μ in diameter, on the polyurethane layer. About 40 m of this adsorber was rolled, and a hemoperfusion column was prepared therewith as shown in FIGS. 3 and 4. The adsorber housed in the column contained about 80 g of activated carbon.

The whole blood of dogs was passed through this hemoperfusion column at a flow rate of 50 ml/min, and its pressure was observed at the inlet and the outlet of the column. The pressure diference, i.e. pressure loss in this case was found to be 15 mmHg. Such a small pressure loss will not cause hemolysis. In contrast, the pressure loss observed in the case of a commercially available hemoperfusion column packed with granular activated carbon reached as high as 100 mmHg. However, there was very little difference between the two cases in the amount of carbon dust occurring. Thus, the adsorber in this invention can be used safely for hemoperfusion.

What is claimed is:

1. A method for removing soluble poisonous substances contained in blood by hemoperfusion comprising providing a support;

attaching a porous membrane to said support, said membrane having a thickness in the range of approximately 10–400 microns and containing a powdery or fine particulate adsorbent for removing soluble poisonous substances from blood; and bringing blood into contact with said adsorbent-containing membrane, thereby effectively removing said poisonous substances from said blood.

2. The method of claim 1 further comprising the steps of:

placing said adsorbent containing porous membrane and support in a housing containing a blood inlet and a blood outlet; and passing blood through said housing via said blood inlet and outlet.

3. The method of claim 1 wherein said adsorbent has an average particle diameter ranging from about 10 to 100 microns.

4. The method of claim 1 wherein said adsorbent is activated carbon.

5. The method of claim 1 wherein said adsorbent is a porous organic resin.

6. The method of claim 1 wherein said adsorbent is porous alumina.

7. The method of claim 1 whrein said adsorbent is porous silica.

8. The method of claim 1 wherein said adsorbent is porous glass.

9. The method of claim 1 wherein said adsorbent comprises polyurethane.

10. The method of claim 1 wherein the porous membrane contains the adsorbent in the range of from 30 to 70 wt%.

11. A method for removing soluble poisonous substances contained in blood by hemoperfusion comprising the steps of providing a porous membrane having a thickness in the range of approximately 10–400 microns and containing a powder or fine particulate adsorbent for removing soluble poisonous substances from blood;

wrapping said membrane about a core;

placing said core in a housing having a blood inlet and a blood outlet; and passing blood through said housing via said blood inlet and outlet and thereby effectively removing said poisonous substances from said blood.

12. The method of claim 11 further comprising the steps of:

seating annular elastomeric end panels having a porous structure on said core adjacent the opposed ends of said membrane; and seating annular supports on said core between the elastomeric end panels and the blood inlet and blood outlet.

13. A method for removing soluble poisonous substances contained in blood by hemoperfusion comprising the steps of:

preparing an adsorbent membrane having a thickness in the range of approximately 10–400 microns by applying a polymer solution contining an adsorbent dispersed therein to a support, then subsequently contacting the applied solution with a nonsolvent for said polymer; and bringing blood into contact with said absorber thereby effectively removing said poisonous substances from said blood.

14. The method of claim 13 wherein the nonsolvent for said polymer is water.

15. A method for removing bilirubin contained in blood by hemoperfusion comprising providing a support;

attaching a porous membrane to said support, said membrane having a thickness in the range of approximately 10–400 microns and containing a powdery or fine particulate adsorbent for removing bilirubin from blood; and bringing blood into contact with said adsorbent-containing membrane, thereby effectively removing said bilirubin from said blood.

16. A method for removing bilirubin contained in blood by hemoperfusion comprising the steps of:

providing a porous membrane having a thickness in the range of approximately 10–400 microns and containing a powdery or fine particulate adsorbent for removing bilirubin from blood;

wrapping said membrane about a core;

placing said core in a housing having a blood inlet and a blood outlet; and passing blood through said housing via said blood inlet and outlet and thereby effectively removing said billirubin from said blood.

17. A method for removing bilirubin contained in blood by hemoperfusion comprising the steps of:

preparing an adsorbent membrane having a thickness in the range of approximately 10–400 microns by applying a polymer solution containing an adsorbent dispersed therein in a support, then subsequently contacting the applied solution with a nonsolvent for said polymer; and bringing blood into contact with said adsorber thereby effectively removing said bilirubin from said blood.

* * * * *